US008260189B2

(12) United States Patent
Chainer et al.

(10) Patent No.: US 8,260,189 B2
(45) Date of Patent: Sep. 4, 2012

(54) ENTERTAINMENT SYSTEM USING BIO-RESPONSE

(75) Inventors: Timothy Chainer, Putnam Valley, NY (US); Tomasz J. Nowicki, Briarcliff Manor, NY (US); Howard Sachar, Mount Kisco, NY (US); Charles P. Tresser, Nice (FR)

(73) Assignee: International Business Machines Corporation, Armonk, NY (US)

( * ) Notice: Subject to any disclaimer, the term of this patent is extended or adjusted under 35 U.S.C. 154(b) by 1277 days.

(21) Appl. No.: 11/619,369

(22) Filed: Jan. 3, 2007

(65) Prior Publication Data

US 2008/0161109 A1 Jul. 3, 2008

(51) Int. Cl.
*G09B 3/00* (2006.01)
(52) U.S. Cl. ........................................ 434/350
(58) Field of Classification Search .................. 434/350; 463/40–42
See application file for complete search history.

(56) References Cited

U.S. PATENT DOCUMENTS

| 3,855,998 A | 12/1974 | Hidalgo-Briceno |
| 5,333,106 A * | 7/1994 | Lanpher et al. ............... 600/538 |
| 6,623,427 B2 | 9/2003 | Mandigo |
| 7,698,238 B2 * | 4/2010 | Barletta et al. .................. 706/16 |
| 2005/0181347 A1 * | 8/2005 | Barnes et al. .................. 434/350 |
| 2005/0250996 A1 * | 11/2005 | Shirai et al. .................... 600/301 |
| 2007/0124292 A1 * | 5/2007 | Kirshenbaum et al. ........... 707/3 |
| 2008/0081692 A1 * | 4/2008 | Pope et al. ........................ 463/31 |
| 2008/0147439 A1 * | 6/2008 | Maliszewski ..................... 705/2 |
| 2008/0191864 A1 * | 8/2008 | Wolfson ......................... 340/524 |
| 2008/0214903 A1 * | 9/2008 | Orbach ......................... 600/301 |

* cited by examiner

*Primary Examiner* — Masud Ahmed
(74) *Attorney, Agent, or Firm* — McGinn IP Law Group, PLLC (57) ABSTRACT

An entertainment system using bio-response includes a narrative, which includes a plurality of narrative segments assembled into at least one of a plurality of sequences, depending on at least one of a user profile and user bio-response, to create a plurality of cogent narratives.

20 Claims, 5 Drawing Sheets

ENTERTAINMENT SYSTEM USING BIO-RESPONSE

BACKGROUND OF THE INVENTION

1. Field of the Invention

The present invention generally relates to a narrative entertainment or educational system, and more particularly to a method and apparatus for using bio-response to control the sequence of events within a story, game or other work.

2. Description of the Related Art

Sensors and bio-response mechanisms have been used to select entertainment content. Furthermore, certain forms of entertainment media, such as computer games (e.g., "The Oregon Trail"), permit the player to make choices which guide the outcome of events and controls the experienced narrative.

For example, in one conventional system, an entertainment device is programmed according to the response of a user to move the user toward a desired state and to return the user more often to that state of aesthetic experience. This system, however, does not provide the programmed capability to match user responses to narrative events, over varying periods of time, and make judgments as to the narrative direction which will be followed. Indeed, this conventional system does not aim to extrapolate from sensors linked to the user the narrative path that will maximize the effect intended by the narrative composer. In the invention described here, if the intention is to create a frightening story, then the program extrapolates from the current and historic bio-response the path through which the narrative is most likely to frighten the specific individual. Applicants point out, however, that an author of a narrative and program may not wish to maximize the effects at each choice point but may want to have "peaks and valleys" to create the greatest overall effect.

Another conventional system uses bio-response for selecting and providing music and other entertainment products to a user. The system assumes that the creator of the entertainment is unaware of the process of selection, and does not posit the connection of narrative with multiple cogent paths to a biofeedback device enabling distinct and varying narrative works.

While the description above is directed to entertainment examples, the above can also be applied to commercial narratives including, but not limited to, infomercials.

SUMMARY OF THE INVENTION

In view of the foregoing and other exemplary problems, drawbacks, and disadvantages of the conventional methods and structures, an exemplary feature of the present invention is to provide a method and structure in which an author may create multiple cogent paths in a narrative work (e.g., digital video, digital audio, digital text) stored on a direct access media (e.g., DVD or CD) that presents the narrative (e.g., narrative video). A further feature of the present invention is to provide a bio-response mechanism such as a pulse reader, galvanic skin meter, facial expression analyzer or iris measurement gauge that can collect data corresponding to the physical reaction of the viewer. An additional feature of the present invention is to provide computing capability that can process the bio-response and make intelligent choices based on this information to guide the path taken through the video content.

In accordance with a first aspect of the present invention, an entertainment system using bio-response includes a narrative, which includes a plurality of narrative segments assembled into at least one of a plurality of sequences, depending on at least one of a user profile and user bio-response, to create a plurality of cogent narratives. The system described may be entirely local to the user or have portions that are remote.

In accordance with a second aspect of the present invention, a narrative includes a plurality of narrative segments assembled into at least one of a plurality of sequences, depending on at least one of a user profile and user bio-response, to create a plurality of cogent narratives.

In accordance with a third aspect of the present invention, a method of creating a cogent narratives includes assembling a plurality of narrative segments into at least one of a plurality sequences, depending on at least one of a user profile and user bio-response.

Accordingly, elements of a narrative are created which, all or a subset of, can be assembled in multiple ways providing multiple complete and cogent experiences. By means of sensing the user's reactions and/or other means outside the conscious control of the participant(s), the storyline is dynamically assembled. The path of the story is determined during the process of viewing/listening/participating based on the physical reactions of the user(s) and/or based on their past response to similar stimuli.

In accordance with an exemplary feature of the present invention, a viewer/participant is able to customize the experience of a narrative (story, game, educational material, etc.) based on bio-response. In this way each engagement with the narrative may be different and perhaps surprising. The present invention provides an integral linkage between the narrative and the biofeedback. The narrative in this invention has been expressly created to be experienced by a user who is linked or has been linked to bio-feedback sensors and, based on the intelligent processing of the sensor information, one path among many possible paths through the narrative is experienced by the user. The narrative's author creates the content aware that multiple narratives will be experienced and that there are a known set of choice points.

An additional feature of the present invention is that the choices are made by the user but not exclusively by conscious means. They are made by the intelligent processing of user input and bio-response information. This information may be collected from the user during the experience of the narrative, it may be collected prior to the experience, or information may be combined from before and during the narrative experience. The system may combine the bio-response information from multiple users in influencing the course of the narrative which may be experienced by multiple users. The bio-response information may be combined with other information including information consciously provided by the user(s) and random information.

BRIEF DESCRIPTION OF THE DRAWINGS

The foregoing and other exemplary purposes, aspects and advantages will be better understood from the following detailed description of an exemplary embodiment of the invention with reference to the drawings, in which.

DETAILED DESCRIPTION OF EXEMPLARY EMBODIMENTS OF THE INVENTION

Referring now to the drawings, and more particularly to FIGS. 1-4 there are shown exemplary embodiments of the method and structures according to the present invention.

The invention creates a human-machine interaction in which works are created with multiple cogent alternative narratives and, based on feedback from the input both inside and outside the conscious control of the participants, the progress of the experienced event is determined. The present invention addresses ways to vary and improve the experience of narratives and offers a means of better understanding the user's preferences.

The present invention links processed bio-response with the path of the narrative. Many video and computer games have multiple cogent paths that are chosen based on conscious decisions made by the user(s). They may in addition have some randomizing features. In the system of the present invention the narrative path is determined by the user(s) but based on information not entirely under their control.

For example, assume the intention is to create an entertainment video intended to frighten people (i.e., a "horror" movie). The video is made up of multiple discrete scenes. Each individual finds different things particularly frightening (e.g., spiders, snakes, shadowy characters, etc.). The individual's reaction to these images/effects are reflected in changes in their physical being (e.g., pulse, iris size, breathing, etc.) that may be recorded using bio-response devices and processed using an intelligent program. This program may among other things post-process the bio-response data, normalize the data, compare the data with previously recorded data, assess the viewers state based on the data and previously recorded or processed data, and assess what segment should be shown based on the intent of the author and knowledge of the viewer. With this scheme bio-response information is processed and, based on the outcome, the narrative (i.e., the plot of the horror movie) is customized to optimize the experience for the specific viewer.

For instance, a character in the narrative may open a door to a room. The scene that appears once the character enters the room is selected from multiple options based on the processing of the bio-response information gathered via gauges connected to the viewer prior to this "choice point" in the presentation of the narrative. The outcome is a narrative that is customized to the viewer's reactions at the time of viewing. The same viewer is likely to see a different horror movie the next time if the user's physical reaction changes.

Another example of the use of this invention is to dynamically edit works based on the user profile which has been generated by their past reaction to other works and/or dynamically as described above. For instance, specific aversions (e.g., animal cruelty) may be detectable from bio-response. These aversions can be recorded and profiled. When new material is presented, the system dynamically edits the presentation to eliminate offending scenes from view. In this case skipping scenes may be viewed as an alternative narrative.

The present invention can be used to better understand the customer of a service, and to offer the customer better services and products of all sorts. Based on analysis of the chosen paths and the overall satisfaction of the user, knowledge of preferences can be discerned.

The present invention may be used to gather responses for the purpose of understanding potential offerings beyond narratives. For example, the appearance of a product and the circumstances of use which is most appealing may be measured within complex narratives.

The present invention may be used for educational purpose to match the most effective means of presenting a narrative to a specific audience dynamically based on the reaction of the audience to portions of the presentation.

Figure 1:
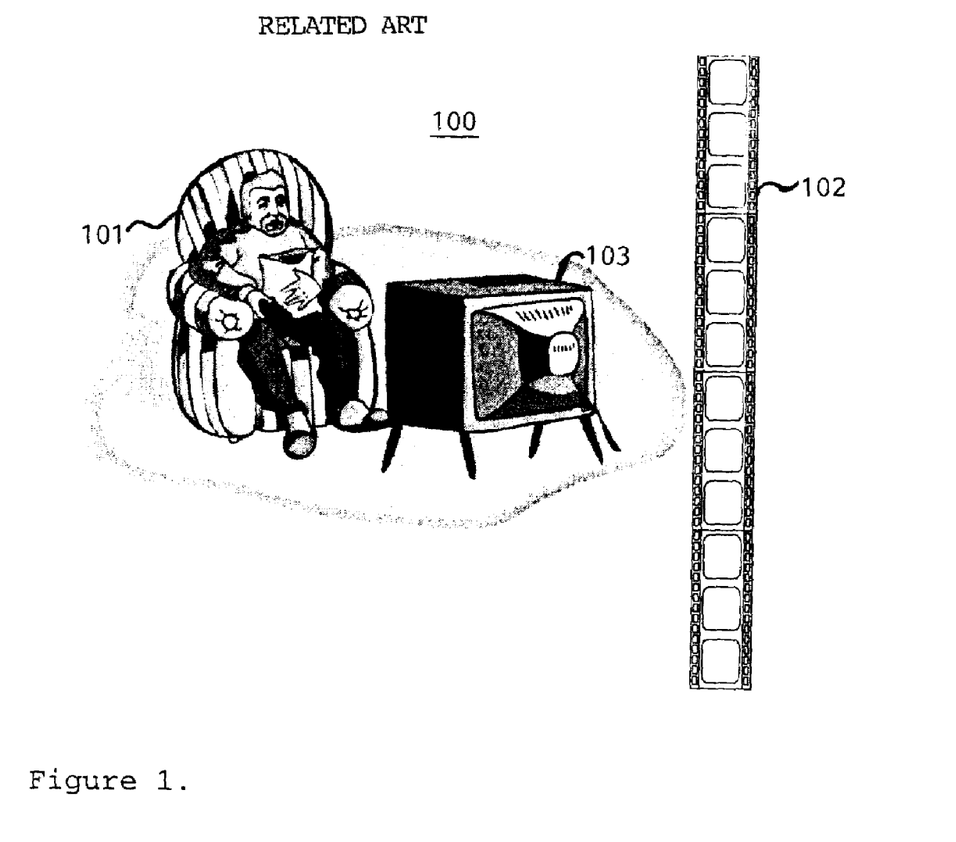
FIG. 1 illustrates a conventional viewer interaction 100 with entertainment media.

FIG. 1 depicts the conventional method 100 for a user to watch a video narrative. Simply, the user 101 merely watches the video narrative 102 in its existing sequence on a television 103.

Figure 2A:
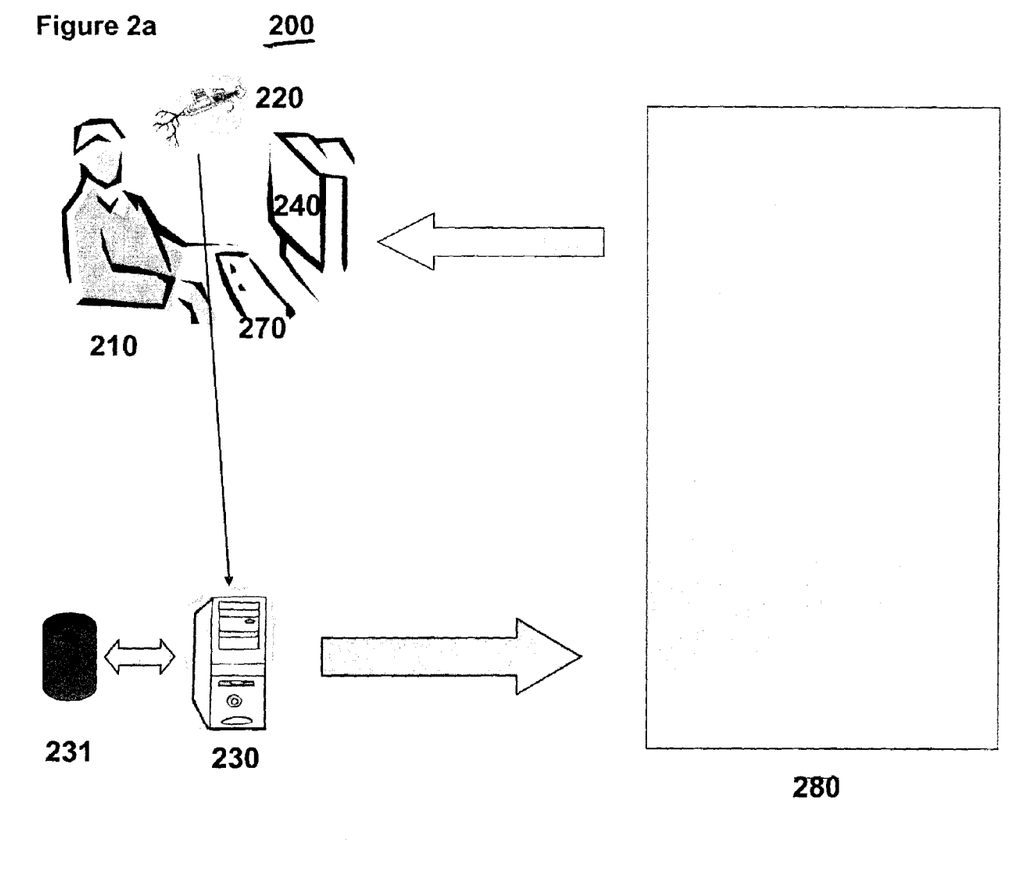
FIG. 2a illustrates a sensory entertainment system 200 using bio-response in accordance with an exemplary embodiment of the present invention.

FIG. 2 depicts a sensory entertainment system 200 using bio-response in accordance with an exemplary embodiment of the present invention.

The system 200 provides a linkage between bio-response of a user 210 and a video narrative. The system includes a bio-monitor device 220 that is capable of measuring biological responses of the user 210. The bio-monitor 220 may include one or a plurality of bio-sensors and/or recording devices. The bio-sensors may measure, but are not limited to measuring, heart rate, pupil dilation, skin sensitivity, breathing and muscle measurement. Specifically, the bio-monitor may include at least one of (but is not limited to) a pulse reader, a galvanic skin meter, and an iris measurement gauge. It may also include indirect means such as video recording of facial muscle movements of the user to interpret the emotional state of the user as a result of a specific segment of the narrative.

The bio-monitor 220 transmits the bio-response data to a processing device 230 (e.g., a central processing unit (CPU)). The processing device, using a processing software program, processes the bio-response data and triggers changes in the narrative path based on the bio-response data by sending commands (232; see FIG. 2b) to the media player 280 which responds by sending the appropriate content to the display 240. For example, the processing may include an analysis of the recorded user facial movements to determine an emotional reaction. Additionally, the user's bio-response data may be stored in a historical database on the DASD 231 for later use.

Figure 3:
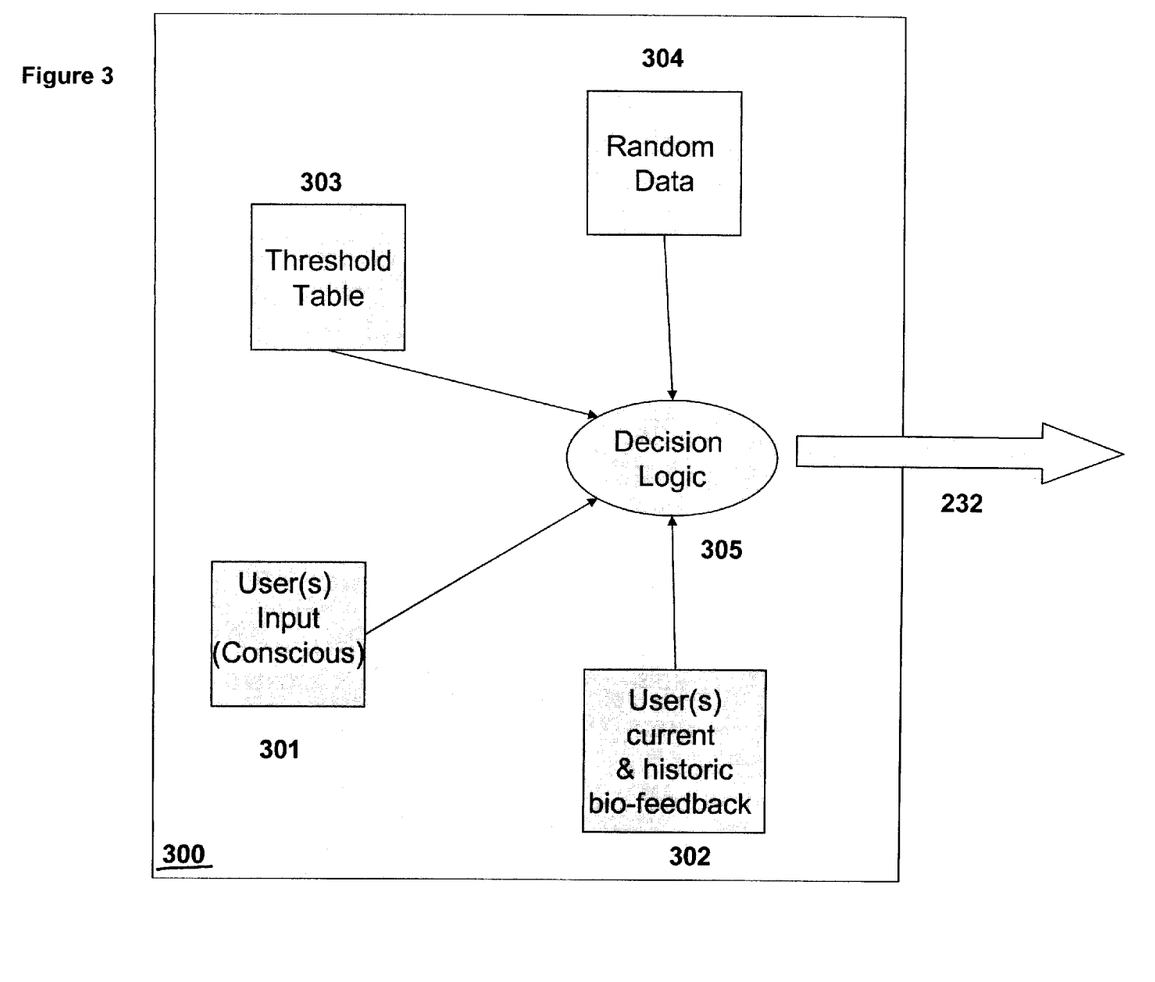
FIG. 3 illustrates a decision logic 300 of the sensory entertainment system 200.

FIG. 3 depicts the main logical elements 300 that support the intelligent processing software. Previously collected bio-response data from prior user experiences stored in the historical database may be used to influence how the sequence or attributes of a story are assembled. Furthermore, knowledge of the user's past bio-reactions may be used to calibrate the intensity of reaction to current stimuli and may be used to determine the narrative experience. The past data stored in the historical database may be used in combination with current bio-response data to determine the sequence of a narrative.

Associated with each narrative segment is an author evaluation which is used in determining the suitability of that segment with respect to a plurality of criteria. Together these evaluations form a threshold table, which is used to restrict which narrative sequences can be presented to a specific user. The table is an authoring tool by which means the author orchestrates the overall potential experiences of the work.

The decision logic 305, in generating the commands 232 that determine the course of the narrative, includes one or more of previously obtained knowledge of user preferences, including input provided consciously by user 301, and user current and historic bio-responses 302. In addition, random data components 304 can be introduced to vary the user experience, for example, if the narrative is viewed more than once. Furthermore, the authors input their views into the decision logic by providing a threshold table 303 of the authors' expectations for each narrative segment.

Referring again to FIG. 2a, the processing device 230 receives data from the bio-monitor 220 or the DASD 231. The processing device calculates an overall bio-sensor score, which is used to determine the sequence and intensity of the narrative.

The system 200 includes a display device 240 (e.g., monitor) for the viewer 210 to experience the video narrative. The display device 240 may include multimedia output devices for providing video, audio, fragrance, taste, motion and tactile stimuli.

Figure 2B:
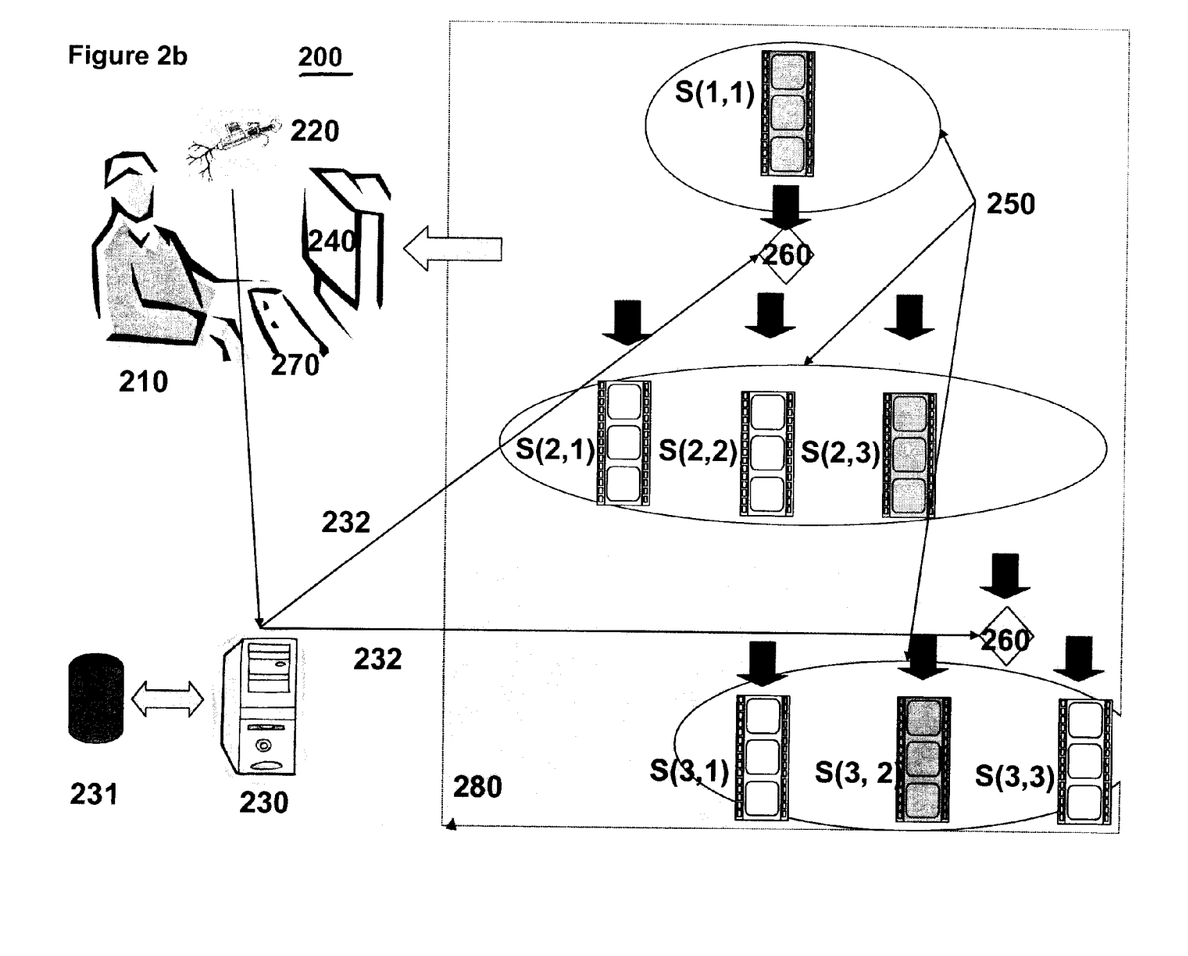
FIG. 2b illustrates the subcomponents of the sensory entertainment system 200.

As depicted in FIG. 2b, each video narrative in the system 200 includes a plurality of narrative segments 250 that can be assembled in a plurality of sequences, depending on the bio-response of the user 210, to create one of a plurality of possible cogent narratives. Each narrative includes a plurality of choice points 260 where, based on the processed bio-response data, the sequence of the narrative may be altered.

The system 200 may include a user input device 270 (e.g., a computer keyboard and mouse). Through the input device 270, the user 210 may select the emotional states and the degree of emotional state that the user 210 may wish to experience. The information input by the user 210 is also used to control the narrative sequence and the intensity of emotional states attained. This is an example of the conscious input 302 that is used in the process of deciding the narrative segment to be presented.

An example of implementation of the invention is described below. As shown in FIG. 2b, the narrative can be viewed as a lattice in which there are segments and branch points. A cogent narrative is a path through the lattice to a terminating segment (as defined later).

The following variables are defined:

UI(j) is a user profile given as a vector of numeric values that represents the user's previously ascertained aversions and/or preferences. For example a user profile may look like
UI(1)=0 Strong Aversion to Snakes
UI(2)=0.5 Mild Aversion to Violence
UI(3)=1 Strong Preference to Romance In this example, a range of 0 to 1 is used to rate a user aversion or preference. A low score suggests a user aversion and a high score suggests a user preference.

UP represents a user profile, which in one example may be calculated from both the user input and stored biometric data (SBF) as defined below. For example, UP(j)=(Alpha×UI(j)+Beta×SBF(j)) where Alpha and Beta are non-negative numbers, which sum up to 1. UP as a range of 0 to 1.

S(X, N) represents the narrative segment (X, N). SP(X, N, V(j)) represents the segment profile for segment (X, N) represented as a matrix (a threshold matrix) where X is the level in the lattice and N is the label of the branch, and V(j) is the authors anticipated reaction of the user for each selected aversions/preference. SP (End, N, V(j)) defines a final segment in one of the possible narratives. This is referred to as a terminating node, when X=End.

For example, V(1) in SP(2, 1, V(1)) would represent the expected user reaction to the second level Segment 1 with respect to the user aversion to snakes. If for this specific segment V(1)=0, then no negative user reaction is expected for this segment such as the case of absence of snakes. If V(1)=1, then a strong negative user reaction is expected such as showing several snakes. All segments S(X, N) such that the V(j) of their profile SP(X, N. V(j)) is of higher value than the user profile UP(j) (i.e., V(j)−UP(j)>0) are eliminated from the narrative lattice. After the segments are eliminated, a check is performed to confirm there are remaining cogent narratives to terminating nodes.

SBF(j) represents the stored user bio-response data. In one case, SBF(j) may be a simple average of previous bio-response data SBF=Sum for Z=1 to K of (V(j)×EBF(Z,N)/K), which has a range of numeric values between 0 to 1. K is the stored number of segments the user has seen in their history. EBF is defined below.

IBF(X, N) represents the bio-response of the user at the initiation of segment (X, N) represented as a vector of numeric values. The range of the numeric values within IBF are from 0 to 1.

EBF(X, N) represents the bio-response of the user at the end of segment (X, N) represented as a vector of numeric values. The range of numeric values within EBF are from 0 to 1. EBF(X, N) may represent the value at the end of the segment or the maximum value attained during the segment or a particular moment determined by the author depending on the implementation.

BFV(X, N) represents the bio-response score for the user of segment (X, N) and is calculated as BFV (X,N)=(EBF(X, N)−IBF (X,N)+1/2), and has a range from 0 to 1.

CV(X,N) is a calculated score based upon BFV, a random value and historical bio-response data SBF. For example, CV (N,X)=(Delta×BFV(X,N)+Iota×Random Number (from 0 to 1)+Kappa×SBF(X,N)), where Delta, Iota and Kappa are non-negative numbers, which sum to 1. CV has a value in a range from 0 to 1.

Figure 4:
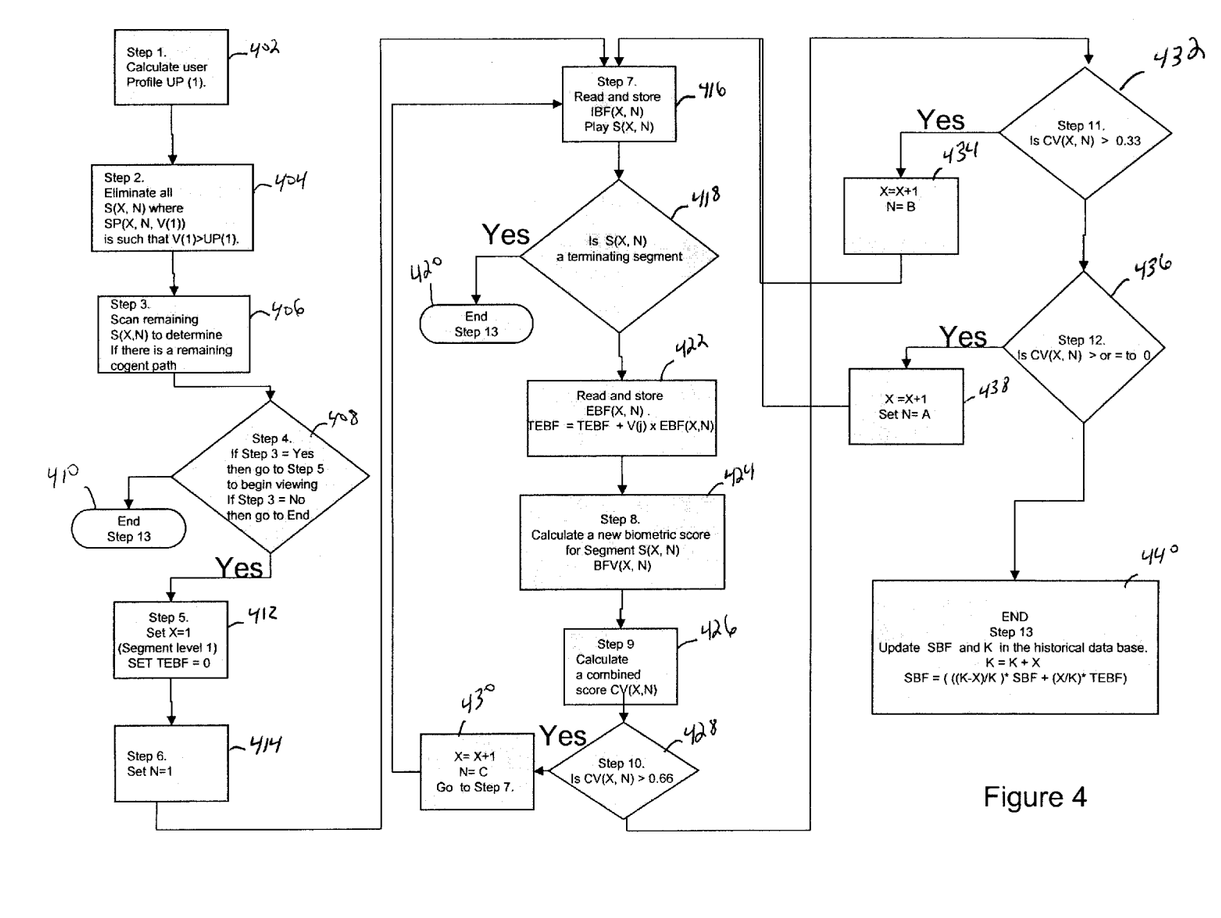
FIG. 4 illustrates an exemplary sequence 400 of viewing a narrative by a user.

A sequence of viewing a narrative is described below and is illustrated in FIG. 4. In this example UP, EBF, and BFV each are one dimensional (i.e., have only one element) and S(X,N) has only three segments per level X given by S(X,A), S(X,B) and S(X,C).

First, the Profile UP (1) is calculated (e.g., 402). UP(1) may be determined by a combination of user input and previous bio-response data, as defined above.

Next, all S(X, N) are eliminated where SP(X, N. V(1)) is such that V(1)>UP(1) (e.g., 404). Segments S(X, N) outside the user profile range are then removed.

The system determines if there are remaining cogent narratives (e.g., 406 and 408), that is one or more paths through the lattice reaching a terminating segment. All segments not within remaining cogent narratives are removed.

If there are no remaining cogent narratives, then the system moves to the end (e.g., 410). If however, there are remaining cogent narratives, the system begins viewing. X is set to equal 1 (segment level 1) (e.g., 412). TEBF is set equal to 0 where TEBF is a variable that represents the sum of EFB during the viewing of the narrative (e.g., 412), and N is set to equal to 1 (e.g., 414).

The initial bio-response IBF (X,N) is read and stored (e.g., 416; referred to as "step 7"). The narrative segment S(X,N) is then played. If S(X,N) is a terminating segment (e.g., 418), then the system moves to the end (e.g., 420). If not, then the final bio-response for this segment EBF(X,N) is then read and stored (e.g., 422). TEBF is undated (i.e., TEBF=TEBF+V(j)×EBF(X,N)) (e.g., 422).

A new biometric score BFV(X,N) is calculated for segment S(X, N) (e.g., 424), as described above. Then, the combined score CV(X,N) is calculated (e.g., 426, as described above. It is then determined if CV(X,N) is greater than 0.66 (e.g., 428). If CV(X,N) is greater than 0.66, X is set to equal X+1, N is set to equal C and the process returns to step 7 (e.g., 416).

It is then determined if CV(X,N) is greater than 0.33 (e.g., 432). If CV(X,N) is greater than 0.33, then X is set to equal X+1, N is set to equal B (e.g., 434) and the process returns to step 7 (e.g., 416). If CV(X,N) is not greater than 0.33, the process continues.

Next, it is determined if CV(X,N) is greater than or equal to 0 (e.g., 436). If CV(X,N) is greater than or equal to 0, then X is set to equal X+1, N is set to equal A (e.g., 438) and the process returns to step 7 (e.g., 416). If CV(X,N) is not greater than or equal to 0 then the process ends (e.g., 440). Additionally, SBF and K are then updated in the historical database (e.g., 440). K is set to K+X and SBF is set to ((K−X)/K×SBF+(X/K)×TEBF).

Using the above process flow we describe an illustrative example. For purposes of illustration it is assumed that a scale for "fear of snakes" is between 0 to 1 where 1 is the most frightening. It is also assumed that this is the only basis for determining which segments are viewed. It is also assumed that there is one source of bio-response and that value reflects the viewer's fear reaction relative to snakes and the user input UI(1) of 0.8. It is also assumed that Alpha and Beta=0.5, Delta=Kappa=0.5 and Iota=0, as there are no random effects. It is also assumed that the value of SBF(1) is 0.6 and K=8. In this case, for all SP(X,N,V) the value of V is set by the author to be 0.65. All of the segments are checked and confirmed that V(1) is less than UP(1), therefore no segments are eliminated.

At step 1 (402), the user profile is calculated as UP=(0.5×0.8)+(0.5×0.6)=0.7, thus, no segments are eliminated (e.g., step 2 (404)) because V(1)=0.65, which is less than UP(1)=0.7.

At step 3 (406), it is determined that the viewer can proceed to see the narrative. Viewing is then begun (step 408). X is set equal to 1 and TEBF is set equal to 0 (step 5 (412)). Then, N is set equal to 1 (step 6 (414)).

In step 7 (416), the bio-response IBF (1, 1) is assumed to be zero and the segment played. It is assumed that EBF(1,1) is equal to 1 and TBEF is calculated to be equal to 0.65 (i.e., EBF(1,1)=0+0.65×1).

In step 8 (424), based on the calculated value from processor 230 BFV(1, 1)=(1−0+1)/2=1.

In step 9 (426) the combined score is calculated as CV(1, 1)=0.5×1+0×Random+0.5×0.6=0.8 (recall that it has been assumed that there is no random effect in this example). Thus, CV(1,1) is greater than 0.66, so X is set equal to 2 and N is set equal to C, which is equal to 3 (428).

The process then returns to step 7 (416). The process continues until a terminating segment is viewed and following the viewing the stored biometric information SBF and K are updated (440).

While this process is described for a single user, a group score can be determined in a similar manner for multiple users in which each users' profile UP and biometric score BFV is calculated and combined. For example, a total user profile could be calculated as:

$$UP(\text{total})=(UP(\text{user 1})+UP(\text{user 2})+UP(\text{user 3}))/3.$$

A similar math average for biometric effects may also be created. By using a total score the group may determine the experience of the narrative. Obviously other more complex combinations of user profile and biometric scores can be created based on needs of individuals in the audience such as watching a movie with children present. One example is to set UP (Total) as the minimum value of the groups of users with individual UP's such that an experience is eliminated from the narrative.

The method and system of the present invention, which is described above in the context of entertainment video media such as movies and video games, may also be used for educational purpose. That is, the diversity of learning styles can be sensed by the reactions of viewers and then the educational material may be customized to accommodate the individual viewers.

Additionally, the present invention may be used in training for critical situations. For example, certain skills exist that are needed to exercise under situations of pressure (e.g., emergency medical procedures, fire fighting, military and/or police actions, etc.). Training requires both gaining skills and also being able to perform under a variety of stressful conditions. The present system would enable training, which can detect what situations are most stressful for the specific student and focus the learning experience accordingly.

While the invention has been described in terms of several exemplary embodiments, those skilled in the art will recognize that the invention can be practiced with modification within the spirit and scope of the appended claims.

Further, it is noted that, Applicants' intent is to encompass equivalents of all claim elements, even if amended later during prosecution.

What is claimed is:

1. A narrative comprising:
a plurality of video narrative segments assembled into at least one of a plurality of sequences, depending on a user profile and user bio-response to at least one of visual or auditory stimuli in the video narrative segments, to create a plurality of cogent narratives,
wherein a sequence of the narrative is determined while a user is viewing the narrative.

2. The narrative according to claim 1, wherein at least one of said plurality of cogent narratives is selected for at least one of an education application, an entertainment application and a marketing application.

3. The narrative according to claim 1, wherein said plurality of video narrative segments are assembled into said at least one of a plurality of sequences, depending on a plurality of users' profiles and bio-response data.

4. The narrative according to claim 3, wherein said plurality of users' profiles and said bio-response data are weighted to produce the plurality of cogent narratives.

5. The narrative according to claim 1, wherein said plurality of video narrative segments can be assembled into at least one of a plurality of sequences, depending on a threshold table determined by an author of said narrative.

6. An entertainment system using bio-response, comprising:
a video narrative, said video narrative comprising:
a plurality of video narrative segments assembled into at least one of a plurality of sequences, depending on a user profile and user bio-response to at least one of visual or auditory stimuli in the video narrative segments, to create a plurality of cogent narratives,
wherein a sequence of the narrative is determined while a user is viewing the narrative.

7. The system according to claim 6, further comprising:
a bio-response recording device capable of recording a bio-response from a user of the entertainment system;
a processing device that receives bio-response data transmitted from said bio-response recording device, said processing device processes the bio-response data using a processing software program contained in said processing device to trigger changes in the sequence of the video narrative based on the bio-response data; and
a media player that receives commands, from the processing device, which determine which segment of a narrative is experienced by the user.

8. The system according to claim 6, further comprising:
a bio-response recording device capable of recording a bio-response from a user of the entertainment system.

9. The system according to claim 6, further comprising:
a bio-response recording device capable of recording a bio-response from a user of the entertainment system; and
a processing device that receives bio-response data transmitted from said bio-response recording device, said processing device processes the bio-response data using a processing software program contained in said processing device to trigger changes in the sequence of the video narrative based on the bio-response data.

10. The system according to claim 9, further comprising:
a media player that receives commands from the processing device which determine which segment of a narrative is experienced by the user.

11. The system according to claim 9, further comprising:
a historical bio-response database, contained in said processing device, for storing said bio-response data for a later use, said bio-response data stored in said historical bio-response database is used with currently recorded bio-response data to determine the sequence of a narrative.

12. The system according to claim 10, wherein said media player comprises a display device for experiencing the narrative to the user, said display device comprising:
a monitor; and
a plurality of sensory output devices for providing at least one of audio stimuli, fragrance stimuli, taste stimuli, motion stimuli and tactile stimuli.

13. The system according to claim 9, further comprising:
an input device through which the viewer selects emotional states and an intensity degree of the emotional states that the viewer wishes to include in the video narrative.

14. The system according to claim 6, wherein said plurality of video narrative segments are assembled into said at least one of a plurality of sequences, depending on a plurality of users' profiles and bio-response data.

15. The system according to claim 6, wherein said plurality of video narrative segments can be assembled into at least one of a plurality of sequences, depending in whole or in part on a threshold table determined by an author of said narrative.

16. The entertainment system according to claim 6, wherein said video narrative comprises a story and each of said plurality of video narrative segments comprises a segment of the story.

17. The entertainment system according to claim 6, wherein the video narrative further comprises a plurality of predetermined choice points, and
wherein at each of said choice points the entertainment system selects one of said plurality of video narrative segments based on the user profile and the user bio-response to determine the sequence of the video narrative.

18. A method of creating a cogent narrative, comprising:
presenting a plurality of video narrative segments to a user;
detecting, using a biosensor, a user bioresponse to at least one of visual or auditory stimuli in the video narrative segments; and
assembling the plurality of video narrative segments into at least one of a plurality sequences while a user is viewing the video narrative segments, depending on the user bio-response.

19. A non-transitory computer-readable medium tangibly embodying a program of machine readable instructions executable by a digital processing apparatus to perform the method for creating a cogent narrative according to claim 18.

20. A method of deploying computing infrastructure, comprising integrating computer-readable code into a computing system, wherein the computer readable code in combination with the computing system is capable of performing the method for creating a cogent narrative according to claim 18.

* * * * *